United States Patent
Harrison et al.

(10) Patent No.: US 6,197,327 B1
(45) Date of Patent: Mar. 6, 2001

(54) DEVICE AND METHOD FOR TREATMENT OF DYSMENORRHEA

(75) Inventors: Donald C. Harrison; James H. Liu; Wolfgang A. Ritschel, all of Cincinnati, OH (US); Roger A. Stern, Cupertino, CA (US)

(73) Assignee: UMD, Inc., Cincinnati, OH (US)

( * ) Notice: Subject to any disclaimer, the term of this patent is extended or adjusted under 35 U.S.C. 154(b) by 0 days.

(21) Appl. No.: 09/079,897

(22) Filed: May 15, 1998

Related U.S. Application Data
(60) Provisional application No. 60/049,325, filed on Jun. 11, 1997.

(51) Int. Cl.[7] .............................. A61F 6/06; A61F 13/02; A61F 6/14

(52) U.S. Cl. ........................ 424/430; 424/431; 424/432; 424/434; 424/443

(58) Field of Search ..................................... 424/434, 435, 424/423, 443, 451, 464, 430, 431, 432

(56) References Cited

U.S. PATENT DOCUMENTS

| | | | |
|---|---|---|---|
| 3,884,233 | 5/1975 | Summey | 128/263 |
| 3,902,493 | 9/1975 | Baier et al. | 128/270 |
| 4,082,881 | 4/1978 | Chen et al. | 424/241 |
| 4,200,101 | 4/1980 | Glassman | 128/285 |
| 4,271,835 | 6/1981 | Conn et al. | 128/270 |
| 4,292,965 | 10/1981 | Nash et al. | 128/260 |
| 4,309,997 | 1/1982 | Donald | 128/270 |

(List continued on next page.)

OTHER PUBLICATIONS

Andersch et al., An Epidemiologic Study of Young Women with Dysmenorrhea, Am. J. Obstet. Gynecol, Nov. 15, 1982, pp. 655–660.

Bowen et al., Comparision of Bromgenac Sodium and Placebo in Women with Primary Dysmenorrhea, Advances in Therapy, vol. 13, No. 3, May/Jun. 1996, pp. 167–177.

Bulletti et al., Targeted Drug Delivery in Gynaecology: The First Uterine Pass Effect Human Reproduction, vol. 12, No. 5, (1997) pp. 1073–1079.

Chien et al., Medicated Tampons; Intravaginal Systeined Administration O Metronidazole . . . Medscape Abstract No. 83009679.

Fedele et al., Dynamics and Significance of Placebo Response in Primary Dysmenorrhea, Pain, 36 (1389) 43–47.

Hargrove et al., Absorption of Estradiol and Progesterone Delivered Via Jergen's Lotion . . . North American Menopause Society, Boston, Sep. 1997, Abstract #97.051.

P.R. Owen, Prostaglandin Synthetase Ingibitors in the Tretment of Primary Dysmenorrhea, Am. J. Obstet. Gynecol., Jan. 1, 1984.

M. Yusoff Dawood, Etiology and Treatment of Dysmenorrhea Seminars in Reproductive Endocrinology, vol. 3, No. 3, Aug. 1985, pp. 283–293.

m. Yosoff Dawood, Nonsteroidal Anti–Inflammatory Drugs and Changing Attitudes Toward Dysmenorrhea, The American Journal of Medicine vol. 84 (Suppl 5A) pp. 23–29.

*Primary Examiner*—Carlos A. Azpuru
(74) *Attorney, Agent, or Firm*—Hana Verny

(57) ABSTRACT

Methods, devices, and compositions for treatment of dysmenorrhea comprise an intravaginal drug delivery system containing an appropriate pharmaceutical agent incorporated into a pharmaceutically acceptable carrier whereby the pharmaceutical agent is released into the vagina and absorbed through the vaginal mucosa to provide relief of dysmenorrhea. The drug delivery system can be a tampon device, vaginal ring, pessary, tablet, suppository, vaginal sponge, bioadhesive tablet, bioadhesive microparticle, cream, lotion, foam, ointment, paste, solution or gel. The system delivers a higher concentration to the muscle of the uterus, the primary site for the dyskinetic muscle contraction, which is the pathophysiologic cause of dysmenorrhea.

23 Claims, 4 Drawing Sheets

U.S. PATENT DOCUMENTS

| | | | |
|---|---|---|---|
| 4,317,447 | 3/1982 | Williams | 128/260 |
| 4,318,405 | 3/1982 | Sneider | 128/263 |
| 4,383,993 | 5/1983 | Hussain et al. | 424/239 |
| 4,405,323 | 9/1983 | Auerbach | 604/285 |
| 4,540,581 | 9/1985 | Nair et al. | 514/415 |
| 4,756,907 | 7/1988 | Beck et al. | 424/85 |
| 4,780,480 | 10/1988 | Dunn | 514/469 |
| 4,789,667 | 12/1988 | Makino et al. | 514/161 |
| 5,084,277 | 1/1992 | Greco et al. | 424/433 |
| 5,201,326 | 4/1993 | Kubicki et al. | 128/832 |
| 5,273,521 | 12/1993 | Peiler et al. | 604/13 |
| 5,295,984 | 3/1994 | Contente et al. | 604/317 |
| 5,387,224 | 2/1995 | Semm | 606/191 |
| 5,393,528 | 2/1995 | Staab | 424/436 |
| 5,651,973 | 7/1997 | Moo-Young et al. | 424/401 |

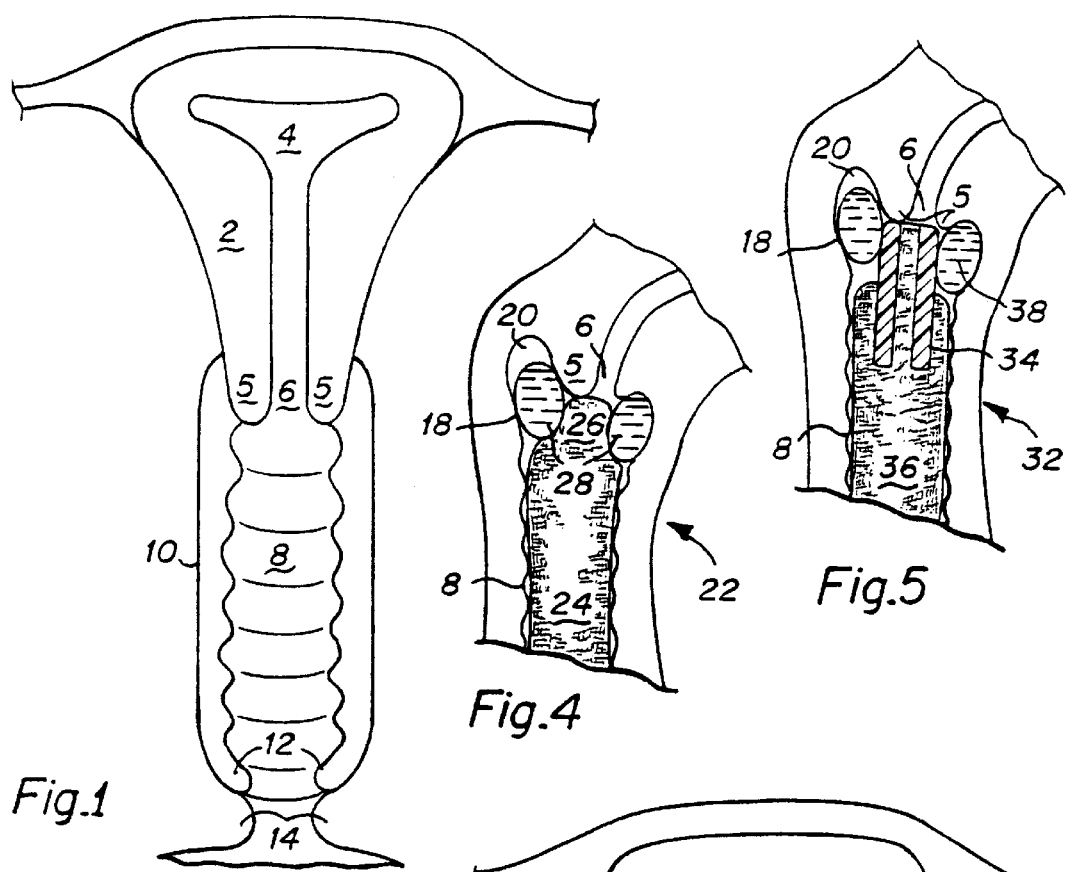
Fig. 1
Fig. 4
Fig. 5
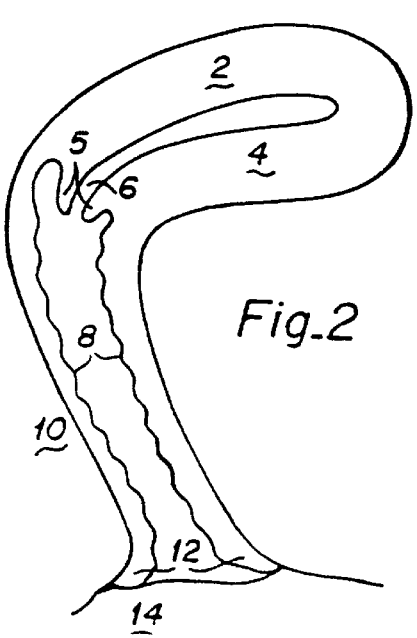
Fig. 2
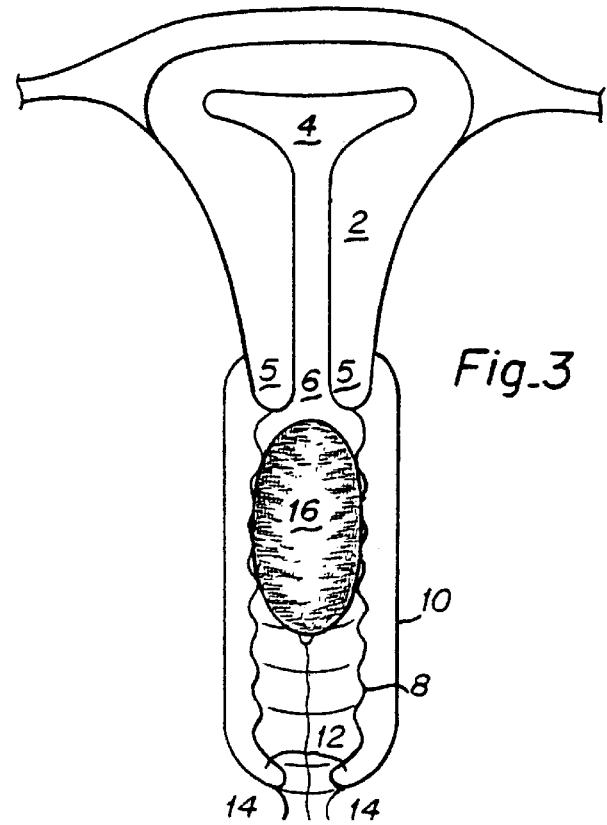
Fig. 3

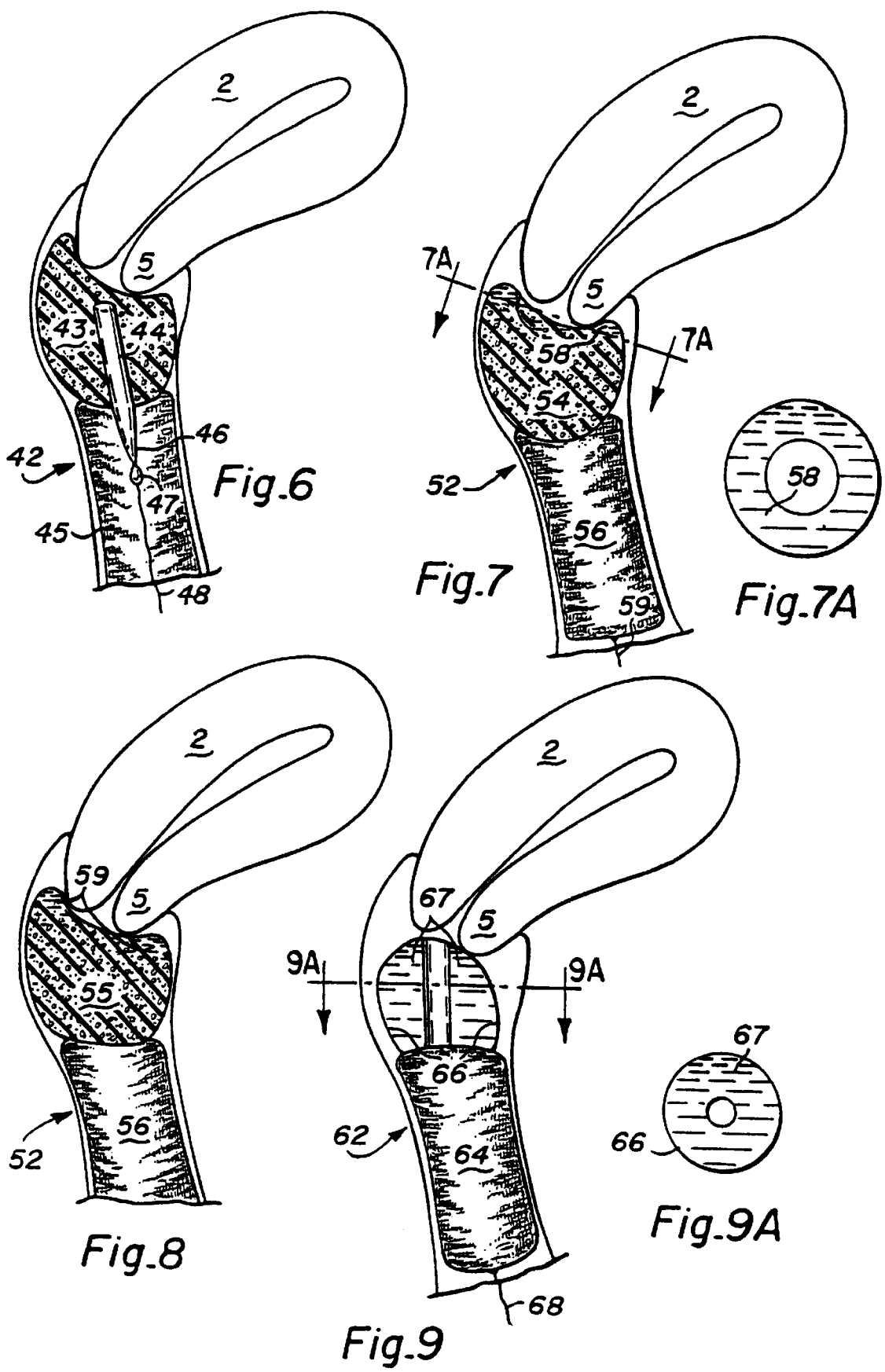

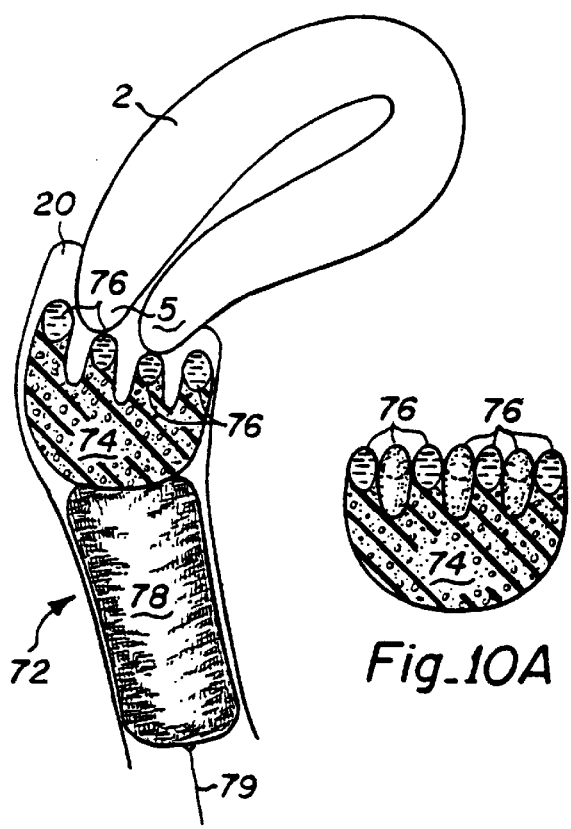
Fig. 10
Fig. 10A
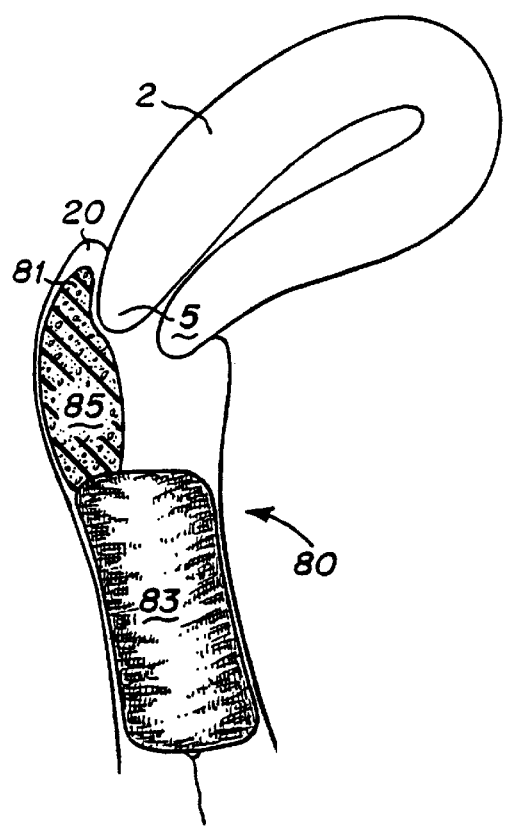
Fig. 11
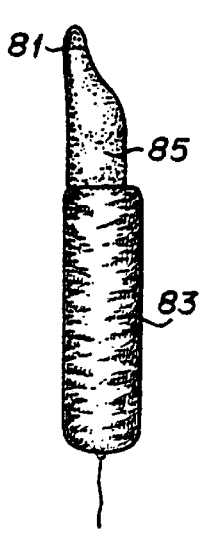
Fig. 12
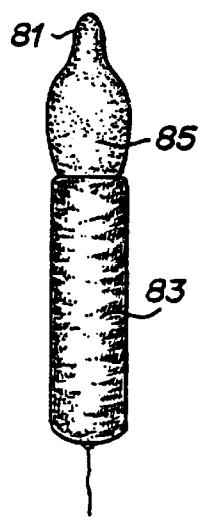
Fig. 13
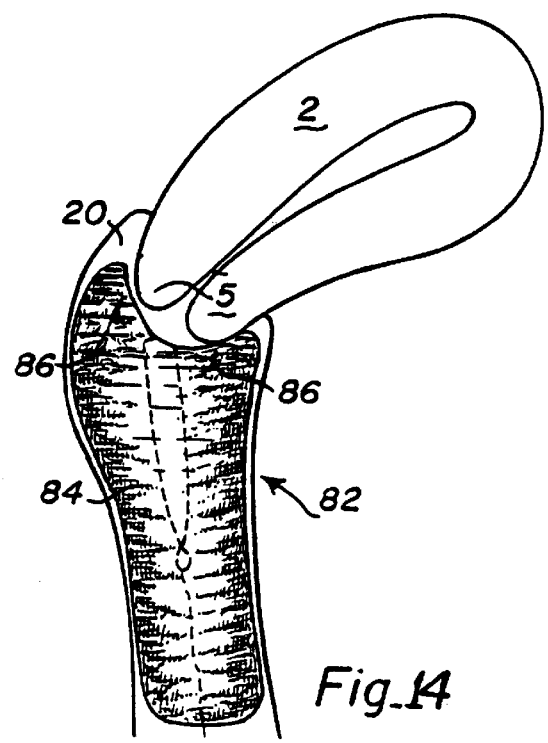
Fig. 14

DEVICE AND METHOD FOR TREATMENT OF DYSMENORRHEA

RELATIONSHIP TO COPENDING APPLICATIONS

This application is a U.S. patent application under 35 U.S.C. §111(a) and claims priority from the copending, commonly assigned provisional application Ser. No. 60/049,325, filed Jun. 11, 1997, under 35 U.S.C. §111(b).

FIELD OF THE INVENTION

The present invention concerns devices, methods, and compositions for treating dysmenorrhea by intravaginal administration of therapeutic and/or palliative drugs to the uterus.

BACKGROUND OF THE INVENTION

Dysmenorrhea, which may be primary or secondary, is the occurrence of painful uterine cramps during menstruation. In secondary dysmenorrhea, there is a visible pelvic lesion to account for the pain, whereas only a biochemical imbalance is responsible for primary dysmenorrhea. Primary dysmenorrhea affects 50 percent of postpubescent women, and absenteeism among severe dysmenorrheics has been estimated to cost about 600 million lost working hours or over 2 billion dollars annually. Thus, an effective, simple, and safe treatment of primary dysmenorrhea over a period of several days during menstruation will not only enhance the quality of life for sufferers of dysmenorrhea, but will have a positive economic impact.

The pain of dysmenorrhea originates in the uterus. Systemic administration of analgesic drugs generally by the oral route to the patient has not successfully relieved the condition in many women and the administration is frequently limited by side effects. We believe this failure is the result of a failure to achieve an effective dosage level of the analgesic to the muscle in the uterus.

SUMMARY OF THE INVENTION

It is therefore an object of the present invention to provide devices, methods and compositions for treating dysmenorrhea by intravaginal delivery of effective doses of drug to the uterus by transvaginal transport to the uterus, that is, into the uterus via lymphatic and venous channels after absorption through the vaginal mucosa.

It is another object of the present invention to provide safe and convenient devices, methods, and compositions which will promote effective localized transvaginal delivery of drugs which are effective to treat dysmenorrhea.

It is another object of this invention to provide pharmaceutically acceptable compositions which will promote effective intravaginal delivery for the purpose of preventing or treating dysmenorrhea.

In one aspect, the present invention provides a method for treating a human female suffering from dysmenorrhea comprising contacting the vaginal epithelium of the female with a pharmaceutical agent selected from the group consisting of nonsteroidal anti-inflammatory drugs, anti-prostaglandins, prostaglandin inhibitors, local anesthetics, calcium channel blockers, potassium channel blockers, β-adrenergic agonists, leukotriene blocking agents, smooth muscle inhibitors, vasodilators, and drugs capable of inhibiting dyskinetic muscle contraction. The agent is in combination with a biocompatible excipient acceptable for application of the agent to the vaginal epithelium. The agent is present in the combination in an amount sufficient to attain a therapeutically effective amount of the agent in the uterine muscle of the individual upon intravaginal application of the combination. In the preferred embodiment, the agent is absorbable through the vaginal mucosa and thereby transmitted via venous and lymphatic channels to the uterus.

Non-limiting examples of nonsteroidal anti-inflammatory drugs suitable for use in the method of the invention include Aspirin, Ibuprofen, Indomethacin, Phenylbutazone, Bromfenac, Fenamate, Sulindac, Nabumetone, Ketorolac, and Naproxen. Examples of local anesthetics include Lidocaine, Mepivacaine, Etidocaine, Bupivacaine, 2-Chloroprocaine hydrochloride, Procaine, and Tetracaine hydrochloride. Examples of calcium channel antagonists include Diltaizem, Israpidine, Nimodipine, Felodipine, Verapamil, Nifedipine, Nicardipine, and Bepridil. Examples of potassium channel blockers include Dofetilide, E4031, Almokalant, Sematilide, Ambasilide, Azimilide, Tedisamil, RP58866, Sotalol, Piroxicam, and Ibutilide. Examples of β-adrenergic agonists include Terbutaline, Salbutamol, Metaproterenol, and Ritodrine. Vasodialtors, which are believed to relieve muscle spasm in the uterine muscle, include nitroglycerin, isosorbide dinitrate and isosorbide mononitrate.

In another aspect, the method of the invention includes combining the pharmaceutical agent with a drug delivery system for intravaginal delivery of the agent. Examples of the drug delivery system include a tampon device, vaginal ring, pessary, tablet, vaginal suppository, vaginal sponge, bioadhesive tablet, bioadhesive microparticle, cream, lotion, foam, ointment, solution and gel.

In one embodiment, the delivery system can be a controlled release drug delivery system. Non-limiting examples of a suitable biocompatible excipient for applying the agent include a lipophilic carrier or a hydrophilic carrier. An example of a suitable carrier is a lipophilic carrier such as semi-synthetic glycerides of saturated fatty acids. Non-limiting examples of a hydrophilic carrier include polyethylene glycol having an average molecular weight of 6000, polyethylene glycol having an average molecular weight of 1500, polyethylene glycol having an average molecular weight of 400 or mixtures thereof. The biocompatible excipient can also include a muco-adhesive agent such as alginate, pectin, or cellulose derivative. The biocompatible excipient can also include a penetration enhancer such as bile salts, organic solvents, ethoxydiglycol, or interesterified stone oil.

In one embodiment of the invention, the excipient comprises between about 60 to 90% by weight lipophilic carrier, between about 5 to 25% muco-adhesive agent, and between about 5 to 20% penetration enhancer.

In another embodiment of the invention, the excipient comprises between about 60 to 90% by weight hydrophilic carrier, between about 5 to 25% muco-adhesive agent, and between about 5 to 20% penetration enhancer.

In another embodiment of the invention, the drug delivery system comprises a standard fragrance free lotion formulation sold under the trademark JERGENS® lotion.

In another embodiment, the biocompatible excipient can include glycerin, mineral oil, polycarbophil, carbomer 934P, hydrogenated palm oil, glyceride, sodium hydroxide, sorbic acid, and purified water.

In another embodiment of the invention, the drug delivery system can be a vaginal suppository which includes 75% SUPPOCIRE® AS2, 10% hydroxypropyl methylcellulose, and 15% TRANSCUTOL®.

In another aspect, the invention provides a device for delivering an effective amount of a pharmaceutical agent to the uterus for treating a human female suffering from dysmenorrhea. The device is an absorbent vaginal tampon device having a proximal and a distal end. Located at the distal end is a means for delivery of the agent to the epithelium of the vagina. The device also includes a means for preferentially conveying fluid discharged from the uterus near the proximal end to the tampon and thereby preventing contact of the fluid with the agent. The device also has a means for retrieval of the device, such as a string or tape as used in tampons, vaginal rings and diaphragms.

In one embodiment, the invention provides a tampon device for delivering a pharmaceutical agent to the uterus comprising an absorbent vaginal tampon having a proximal end and a distal end. A cup-shaped porous foam portion at the distal end fits around the cervix of the uterus and contains a pharmaceutical agent for delivery to the cervix. The device may also include a nonabsorbing axial tube having a distal opening and extending through the porous foam cup into the tampon for conducting blood flow to the absorbent material. A retrieval string or tape connected to the tampon device is also included.

In another embodiment of a tampon device, the distal porous foam cup has a rim which encircles the cervix. The rim has high concentrations of medication and is positioned away from the direct flow of blood which exudes from the cervix during menstruation.

In another embodiment of a tampon device, the distal porous foam up has a rim which encircles the cervix. The rim has fingers extending into the fornix areas around the cervix and the tips of the fingers have high concentrations of medication and are positioned away from the direct flow of menstrual blood.

In another embodiment of a tampon device, a distal porous foam section is in the shape of a scoop, which only partially encircles the cervix. The porous foam scoop has a nib-like shape which is designed to wedge itself into the posterior fornix. The porous foam scoop is designed to deliver medication to the vaginal wall along the entire length of the porous foam scoop.

In another embodiment of a tampon device, distal fibers of the tampon which contact the cervix have high concentrations of pharmaceutical agent for delivery of the agent to the cervical tissue.

In another embodiment of a tampon device, the tampon device has an outer tubing having perforations, the outer tubing is concentric around an axial tube. The device has a distal porous foam section which in its dehydrated state is tight around the outer tubing. A bladder is located proximally to the porous foam and filled with liquid pharmaceutical agent. The bladder is connected to the outer tubing. An outer sheath covers the tampon. The sheath has an annular constriction distal to the bladder such that deployment of the tampon through the distal end of the sheath causes the liquid in the bladder to be forced out distally through the perforated outer tubing and into the porous foam.

In another embodiment of a tampon device, the tampon device has an annular delivery composition around the distal end. The composition contacts the vaginal epithelium for delivery of the agent. A non-absorbing axial tube opens distally and extends into the tampon for conducting blood flow to the absorbent material proximal to the porous foam. The annular composition can be a suppository, foam, paste, or gel.

Embodiments of the invention may include tampon devices of a standard length, or may be longer than standard tampons to facilitate locating the tampon device closer to or in contact with the cervix.

In another aspect, the invention provides a pharmaceutically acceptable composition, in dosage unit form, for intravaginal delivery to a human female for the purpose of treating dysmenorrhea. The composition consists essentially of a combination of an effective amount of a pharmaceutical agent selected from the group consisting of non-steroidal anti-inflammatory drugs, anti-prostaglandins, prostaglandin inhibitors, local anesthetics, calcium channel blockers, potassium channel blockers, β-adrenergic agonists, potassium channel blockers, leukotriene blocking agents, smooth muscle inhibitors, and drugs capable of inhibiting dyskinetic muscle contraction. The agent is combined together with a nontoxic pharmaceutically acceptable carrier. The pharmaceutically acceptable composition can be a vaginal suppository, bioadhesive tablet, bioadhesive microparticle, cream, lotion, foam, ointment, solution or gel.

Non-limiting examples of nonsteroidal anti-inflammatory drugs suitable for use in the composition of the invention include Aspirin, Ibuprofen, Indomethacin, Phenylbutazone, Bromfenac, Fenamate, Sulindac, Nabumetone, Ketorolac, and Naproxen. Examples of local anesthetics include Lidocaine, Mepivacaine, Etidocaine, Bupivacaine, 2-Chloroprocaine hydrochloride, Procaine, and Tetracaine hydrochloride. Examples of calcium channel antagonists include Diltaizem, Israpidine, Nimodipine, Felodipine, Verapamil, Nifedipine, Nicardipine, Piroxicam, and Bepridil. Examples of potassium channel blockers include Dofetilide, E-4031, Almokalant, Sematilide, Ambasilide, Azimilide, Tedisamil, RP58866, Sotalol, and Ibutilide. Examples of β-adrenergic agonists include Terbutaline, Salbutamol, Metaproterenol, and Ritodrine. Vasodialtors, which are believed to relieve muscle spasm in the uterine muscle, include nitroglycerin, isosorbide dinitrate and isosorbide mononitrate.

In one embodiment of the invention, the composition comprises a sustained release gel. In another embodiment, the composition comprises a sustain release suppository.

BRIEF DESCRIPTION OF THE DRAWINGS

FIG. 1 is a cross-sectional representation of a portion of the female reproductive organs including the uterus and vagina in the upright orientation.

FIG. 2 is a cross-sectional side view representation of a portion of the female reproductive organs including the uterus and vagina.

FIG. 3 is the representation of FIG. 1 showing placement of a vaginal suppository in a first embodiment of a drug delivery system according to the present invention.

FIG. 4 is a cross-sectional side view representation of the vaginal area adjacent the cervix showing placement of a first embodiment of a tampon drug delivery system incorporating an annular delivery composition.

FIG. 5 is the representation of FIG. 2 showing placement of a second embodiment of a tampon drug delivery system according to the present invention.

FIG. 6 is the representation of FIG. 2 showing placement of a third embodiment of a tampon drug delivery system incorporating a distal porous foam section.

FIG. 7 is the representation of FIG. 2 showing placement of a fourth embodiment of a tampon drug delivery system incorporating a distal porous foam cup.

FIG. 7A is a cross-sectional view of the embodiment shown in FIG. 7, taken in the direction indicated by the arrows labeled 7A in FIG. 7.

FIG. 8 is an alternate to the embodiment shown in FIG. 7 in which medication is contained in the entire porous foam cup.

FIG. 9 is the representation of FIG. 2 showing placement of a fifth embodiment of a tampon drug delivery system incorporating a distal suppository or gel capsule.

FIG. 9A is a cross-sectional view of the embodiment shown in FIG. 9, taken in the direction indicated by the arrows labeled 9A in FIG. 9.

FIG. 10 is the representation of FIG. 2 showing placement of a sixth embodiment of a tampon drug delivery system incorporating a distal porous foam cup having "fingers."

FIG. 10A is a side view of the distal porous foam cup.

FIG. 11 is the representation of FIG. 2 showing placement of a seventh embodiment of a tampon drug delivery system incorporating a scoop-shaped distal porous foam section.

FIG. 12 is a side view of the embodiment shown in FIG. 11.

FIG. 13 is a front view of the embodiment shown in FIG. 11.

FIG. 14 is the representation of FIG. 2 showing placement of an eighth embodiment of a tampon drug delivery system incorporating distal fibers containing concentrated medication.

DETAILED DESCRIPTION OF THE INVENTION

Figure 15:
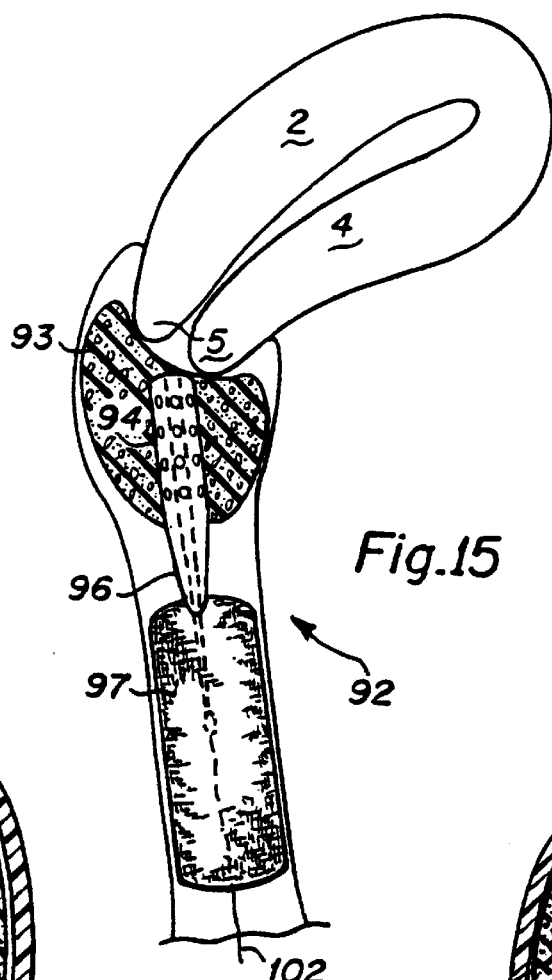
FIG. 15 is the representation of FIG. 2 showing placement of a ninth embodiment of a tampon drug delivery system incorporating non-absorbent tubing having a distal opening.

In reviewing the condition of dysmenorrhea, and the failure of drug treatments applied to this condition, we concluded that limitations due to drug side effects prevented any attempt to overcome the condition by administration through standard routes of higher drug levels to the patient. We believed that the problem could be overcome by focusing the delivery of drug therapy directly to the uterus via the vaginal mucosa, as the uterus is the origin of the painful cramping symptoms of the condition. We hypothesized and have now proven that greatly increased concentrations of therapeutic drugs suitable for treating dysmenorrhea can be obtained by transvaginal delivery through the vaginal mucosa, and we have achieved this delivery by intravaginal application of the drugs through delivery systems of this invention.

In general, the device of the invention comprises a dysmenorrhea treatment agent in a pharmaceutically acceptable, non-toxic carrier combined with a suitable delivery device or system which will effect the transvaginal delivery of the drug to the uterus through the vaginal mucosa.

The systems and methods of the invention have the following advantages over oral administration of drugs: increased concentration of drug delivered to the uterine muscle due to localized delivery; reduction of first-pass metabolism in the liver by avoiding the gastrointestinal system; provision of a continuous drug depot which will provide smooth delivery of drug over a long period of time; and reduction of side effects due to lower systemic concentration. For example, the well established gastro-intestinal side-effects of non-steroidal anti-inflammatory drugs (NSAIDs) do not arise with transvaginal administration as described herein.

The vaginal drug delivery system should provide a sustained delivery of the drug to the vaginal epithelium for the treatment of dysmenorrhea. The delivery system can be a solid object delivery system such as a vaginal ring, pessary, tablet or suppository, for example. Alternatively, it can be a paste or gel having a sufficient thickness to maintain prolonged vaginal epithelium contact. Alternatively, it can be a coating on a suppository wall or a sponge or other absorbent material impregnated with a liquid drug containing solution, lotion, or suspension of bioadhesive particles, for example. Any form of drug delivery system which will effectively deliver the treatment agent to the vaginal endothelium is intended to be included within the scope of this invention.

For purposes of simplifying the description of the invention and not by way of limitation, a suppository drug delivery system will be described hereinafter, it being understood that all effective delivery systems are intended to be included within the scope of this invention.

Pharmaceutical agents for use in the invention are absorbable through the vaginal mucosa. The pharmaceutical agent is preferably selected from the group consisting of nonsteroidal anti-inflammatory drugs (NSAIDs), prostaglandin inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

Preferred NSAIDs include Aspirin, Ibuprofen, Indomethacin, Phenylbutazone, Bromfenac, Sulindac, Nabumetone, Ketorolac, and Naproxen. Preferred local anesthetics include Lidocaine, Mepivacaine, Etidocaine, Bupivacaine, 2-Chloroprocaine hydrochloride, Procaine, and Tetracaine hydrochloride. Preferred calcium channel antagonists include Diltaizem, Israpidine, Nimodipine, Felodipine, Verapamil, Nifedipine, Nicardipine, and Bepridil. Preferred potassium channel blockers include Dofetilide, E4031, Imokalant, Sematilide, Ambasilide, Azimilide, Tedisamil, RP58866, Sotalol, Piroxicam, and Ibutilide. Preferred β-adrenergic agonists include Terbutaline, Salbutamol, Metaproterenol, and Ritodrine. Vasodialtors, which are believed to relieve muscle spasm in the uterine muscle, include nitroglycerin, isosorbide dinitrate and isosorbide mononitrate.

In order to achieve desirable drug release, the active ingredient will be incorporated into an excipient (i.e., vehicle or carrier) for which the drug has low affinity. Hence, hydrophilic drugs will be incorporated into lipophilic carriers, and lipophilic drugs will be incorporated into hydrophilic carriers.

Preferred lipophilic carriers for use with hydrophilic drugs, include semi-synthetic glycerides of saturated fatty acids, particularly from C8 to C18, such as SUPPOCIRE® AS2 (Gattefosse, Westwood, N.J.).

Preferred hydrophilic carriers, for promoting synergistic drug delivery, include polyethylene glycol or mixtures thereof, such as PEG 6000/PEG 1500, or PEG 6000/PEG 1500/PEG 400, or PEG 6000/PEG 400 (Sigma/Aldrich, St. Louis, Mo.).

The system of the invention preferably also comprises a muco-adhesive agent to bring the released drug in solution into prolonged, close contact with the mucosal surface. The muco-adhesive agent is preferably a polymer such as an alginate, pectin, or cellulose derivative. Hydroxypropyl methylcellulose is particularly preferred for use in the present invention.

The system of the invention may also additionally include a penetration enhancer or sorption promoter to enhance permeation of the drug across the uterine mucosal barrier. Preferred sorption promoters include nonionic surface active agents, bile salts, organic solvents, particularly ethoxydiglycol (e.g., TRANSCUTOL® available from Gattefosse), and interesterified stone oil (e.g., LABRAFIL® M 1944CS available from Gattefosse).

Preferred formulations for hydrophilic drugs comprise between about 60–90% by weight lipophilic carrier, between about 5–25% muco-adhesive agent, and between about 5–20% sorption promoter.

In a general method for preparing a formulation including a hydrophilic drug, the lipophilic carrier is melted at 45–50° C. in a heated vessel. The muco-adhesive agent is added to the carrier with stirring. The preferred hydrophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

Preferred formulations for lipophilic drugs comprise between about 50–90% hydrophilic carrier, between about 5–20% muco-adhesive agent, and between about 5–25% sorption promoter.

In a general method for preparing a formulation including a lipophilic drug, the hydrophilic carrier is melted at an appropriate temperature for the particular PEG used in a heated vessel. The muco-adhesive agent is added to the carrier with stirring. The preferred lipophilic drug is dissolved in the sorption promoter, and the drug/sorption promoter solution is added to the carrier/muco-adhesive agent solution. The final formulation is poured into molds of the desired size and shape, which are then placed in a refrigerator at 4–6° C.

The controlled release drug delivery system must be capable of controlled release of a drug into the vagina over several hours or more. During the menstrual cycle, the pH of the vagina changes. Drug delivery systems with buffers to enhance absorption are included in the present invention. The delivery system must be capable of functioning in the presence of menstrual blood and should be easily removable, for example, attached to a string or tape.

Solid phase drug carriers are preferred, because carriers that dissolve or can be diluted out can be carried away by menstrual blood. Advantages of a solid carrier include: 1) no increase in messiness; 2) carrier will not promote bacterial overgrowth with menstrual blood present; 3) carrier may be washable or reusable (e.g., vaginal ring).

The controlled release drug delivery system can be in the form of, for example, a tampon-like device, vaginal ring, pessary, tablet, paste, suppository, vaginal sponge, bioadhesive tablet, bioadhesive microparticles, cream, lotion, foam, paste, ointment, or gel. Each of these systems is discussed below.

FIG. 1 is a cross-sectional representation of a portion of the female reproductive organs, including the uterus and the vagina in the upright orientation, and FIG. 2 is a cross-sectional side view representation thereof. The uterus 2 is a muscular organ enclosing the womb 4, and opening at the cervix 5 via the cervical canal or cervical os 6. The vagina 8 is defined by a muscular tube 10 leading from the labia minora 12 and labia majora 14 to the cervix 5. The local vasculature associated with the walls of the vagina 8 communicate with the uterine muscle vascular and lymphatic systems (not illustrated).

FIG. 3 is a cross-sectional representation of FIG. 1 showing placement of a suppository 16 in the vagina 8 in a position which introduces drugs intravaginally to the uterus 2 by way of the vaginal blood vascular and lymphatic systems (not illustrated).

Referring now to FIGS. 4–12, there being depicted various embodiments of tampon-like devices which can be used to deliver drugs for treatment of dysmenorrhea according to the invention. If a tampon-like device is used, there are numerous methods by which a drug can be incorporated into the device. For example, the drug can be incorporated into a gel-like bioadhesive reservoir in the tip of the device. Alternatively, the drug can be in the form of a powdered material positioned at the tip of the tampon. The drug can also be absorbed into fibers at the tip of the tampon, for example, by dissolving the drug in a pharmaceutically acceptable carrier and absorbing the drug solution into the tampon fibers. The drug can also be dissolved in a coating material which is applied to the tip of the tampon. Alternatively, the drug can be incorporated into an insertable suppository which is placed in association with the tip of the tampon.

The tampon-like device can be constructed so as to improve drug delivery. For example, the tampon can be shaped to fit in the area of the posterior fornix and pubic symphysis and constructed so as to open up to have maximum surface area of contact for drug delivery. If the drug is in a reservoir on the surface of the device, the shape of the device should be such that it can maintain the reservoir towards a vaginal mucosal orientation for best predictable drug release characteristics.

The tampon device can also be constructed so as to have a variable absorption profile. For example, the drug area at the tip of the tampon device could be different from that of the more proximal area in order to force the drug to diffuse out into tissue, as opposed to down into the absorbent part of the tampon. Alternatively, there could be a non-absorbing channel around the cervix for the first centimeter or so in order to minimize menstrual flow from washing away the drug composition.

The release of drug from the tampon device should be timed to provide proper uterine concentration of the drug over a typical length of use of a tampon device, usually 1–8 hours.

FIG. 4 is a cross-sectional representation of the vaginal area, adjacent the cervix 5, with a first embodiment of a tampon drug delivery system according to the invention. The tampon device 22 comprises an absorbent cylindrical tampon 24 comprised of fibrous material, for example cotton, having around its distal end 26 an annular delivery composition 28. The tampon device 22 places the annular delivery composition 28, supported around the distal end 26 of the tampon device 22, against the upper epithelium 18 of the vagina 8 and posterior fornix 20 for delivery through the vaginal surfaces in which the annular composition 28 is in contact. The annular composition 28 can be an annular suppository, foam, paste, or gel composed of suitable delivery components. Since dysmenorrhea occurs just before and during menses, the uterine discharge is absorbed by the tampon 24 and is prevented from carrying away the treatment composition.

FIG. 5 is a cross-sectional representation of the vaginal area adjacent the cervix 5 with a second embodiment of a tampon drug delivery system according to the invention. In this embodiment, tampon device 32 includes a non-porous tube 34 which communicates with the cervical os 6 for delivery of the menstrual discharge from the cervical os to an absorbent cylindrical tampon 36 comprised of fibers, for example cotton, for absorbing the discharge. The tube 34 prevents contact of the discharge with an annular drug delivery composition 38.

FIG. 6 is a cross-sectional representation of the vaginal area adjacent the cervix 5 with a third embodiment of a tampon drug delivery system according to the invention. In FIG. 6, the tampon device 42 includes a distal porous foam section 43 which is in the shape of a cup in the expanded state. In the center of the porous foam section 43 is a non-porous tube 44 which will conduct blood flow to absorbent tampon 45 proximal to the porous foam section 43. The porous foam is preferably a soft, light weight, physiologically inert foam material of polyurethane, polyester, polyether, (e.g., as described in U.S. Pat. No. 4,309,997) or other material such as collagen (e.g., as described in U.S. Pat. No. 5,201,326). The axial tube is preferably a non-absorptive physiologically inert material, such as rubber or plastic, and can be coated on its inner surface with an anticoagulant. The proximal end 46 of the tube 44 has a plastic loop 47 to which a string 48 may be tied for removal of the tampon device 42. The cup-shaped porous foam section 43 fits around the cervix 5 of the uterus 2 and contains medication which may be delivered to the cervical tissue.

FIG. 7 is a cross-sectional representation of the vaginal area adjacent the cervix 5 with a fourth embodiment of a tampon drug delivery system according to the invention. In FIG. 7, the tampon device 52 includes a distal porous foam cup 54 and a proximal absorbent tampon 56. The porous foam cup 54 has a rim 58 which encircles the cervix 5, and which contains high concentrations of medication. The rim 58 area of the porous foam cup 54 is away from the direct flow of blood. The tampon device 52 includes a string 59 for removal of the tampon device 52. FIG. 7A is a cross-sectional view of the embodiment shown in FIG. 7, taken in the direction indicated by the arrows labeled 7A in FIG. 7. As illustrated in FIG. 7A, the rim 58 area forms a ring which contains a high concentration of medication. Alternatively, as illustrated in FIG. 8, the entire porous foam cup 55 may contain medication, not just in the ringed tip area 59 near the cervix 5.

FIG. 9 is a cross-sectional representation of the vaginal area adjacent the cervix 5 with a fifth embodiment of a tampon drug delivery system according to the invention. In FIG. 9, the tampon device 62 includes a proximal absorbent tampon 64 and a distal section 66 which includes a dissolvable suppository or gel capsule 67 filled with liquid medication. The medication prior to dissolution or release of the liquid has a "doughnut" shape to allow for blood to pass through the center of the tampon 64. The tampon device 62 includes a string 68 attached to the tampon 64 for removal of the tampon device 62. FIG. 9A is a cross-sectional view of the of the embodiment shown in FIG. 9, taken in the direction indicated by the arrows labeled 9A in FIG. 9, and illustrates the doughnut shape of the medication filled suppository or gel capsule 67.

FIG. 10 is a cross-sectional representation of the vaginal area adjacent the cervix 5 with a sixth embodiment of a tampon drug delivery system according to the invention. In FIG. 10, the tampon device 72 includes a porous foam distal section 74 which is in the shape of a cup with "fingers" 76 which extend into the fornix areas 20 around the cervix 5. The tips of the fingers 76 contain high concentrations of medication which may be delivered to areas away from the direct flow of blood as the blood moves into absorbent tampon 78 proximal to the cup-shaped porous foam distal section 74. The tampon device 72 includes a string 79 for removal of the tampon device 72. FIG. 10A is a side view of the porous foam cup 74 and illustrates the fingers 76 which extend into the fornix areas 20 around the cervix 5 (FIG. 10).

It will be readily apparent to a person skilled in the art that the characterization of the drug delivery device as having an annular shape is only an approximate description of the shape formed by fluid or semisolid drug delivery devices positioned around a cylinder and in contact with adjacent vaginal wall epithelium, and all shapes which conform to the vaginal epithelium and external cervical surfaces are intended to be included within and indicated by the term "annular". Moreover, use of the term "annular" does not restrict the invention to the use of such devices which encircle the entire cervix (i.e. 360 degrees). Devices which span an angle of less than 360 degrees, but which make sufficient contact with the vaginal epithelium to deliver sufficient quantity of the drug are within the scope of the invention.

The annular drug delivery composition 28, 38 can be an absorbent material which expands in the presence of fluid or body heat to completely fill the space between the tampon 22, 32 and the vaginal epithelium 18.

FIG. 11 illustrates such a drug delivery device having an annular shape which does not completely encircle the entire cervix. FIG. 11 is the representation of FIG. 2 showing placement of a seventh embodiment of a tampon device 80 incorporating a scoop-shaped porous foam section 85. FIG. 12 is a side view of the tampon device 80 and FIG. 13 is a front view of the tampon device 80. The scoop-shaped porous foam section 85 is annular in shape, but does not completely encircle the cervix 5. Instead, the scoop-shaped porous foam section has a nib-shaped tip 81 which is designed to wedge itself into the posterior fornix 20. The scoop-shaped porous foam section 85 is designed to deliver medication to the vaginal wall along the entire length of the scoop-shaped porous foam section 85.

FIG. 14 is a cross-sectional representation of the vaginal area adjacent the cervix 5 with an eighth embodiment of a tampon drug delivery system according to the invention. In FIG. 14, the tampon device 82 comprises an absorbent tampon 84. The section 86 of the tampon 84 which rests against the cervix 5 contains high concentrations of medication. As the fibers absorb fluid, the tampon 84 expands around the cervix 5 and delivers medication to the tissue. The blood will be drawn to proximal sections of the tampon 84 as fibers become more absorbent in this area. The tampon device 82 includes a string 88 for removal of the tampon device 82.

Suitable cylindrical cartridge containers or inserter tubes which assist in the insertion and storage of the tampon systems of the present invention will be apparent to those skilled in the art of tampon construction. Examples are described in U.S. Pat. Nos. 4,3178,447; 3,884,233; and 3,902,493.

In general practice, a drug delivery tampon device as described herein is placed into the vagina and the inserter tube is removed. The tampon device contacts the inner wall of the vagina and the penetration enhancer and mucoadhesive act to facilitate the adsorption of the drug into the local vasculature. This results in a higher concentration of the drug being delivered to the uterine muscle where it acts to minimize the pain of dysmenorrhea.

Figure 16:
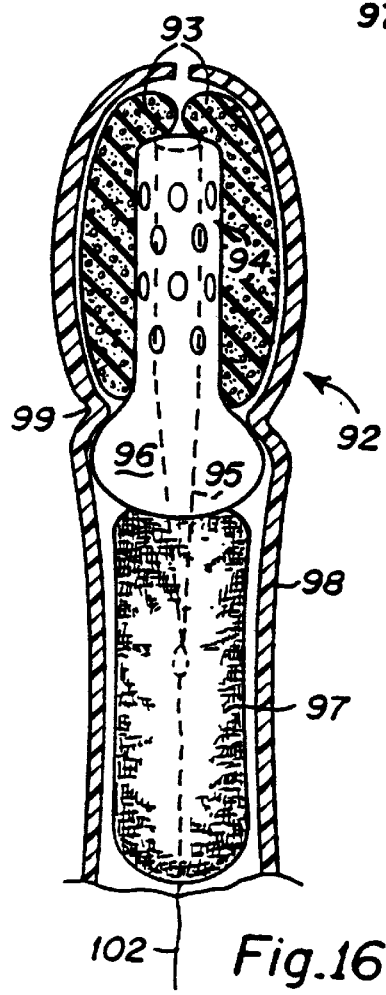
FIG. 16 is the tampon drug delivery system of FIG. 15 in a dehydrated, sheathed, state.
Figure 17:
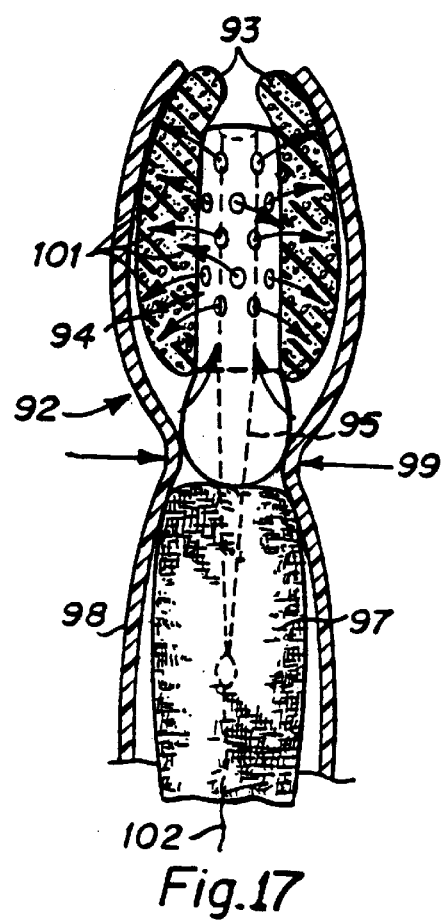
FIG. 17 is the tampon drug delivery system of FIG. 16 showing deployment of the tampon.

FIG. 15 is a cross-sectional representation of the vaginal area adjacent the cervix 5 with a ninth embodiment of a tampon drug delivery system according to the invention. In FIG. 15, the tampon device 92 includes a distal porous foam section 93 which, in its dehydrated, sheathed state (FIG. 16), is tight around a perforated outer tube 94. The perforated outer tube 94 is connected to a bladder 96 located proximally which is filled with liquid medication (not illustrated). Within the perforated outer tube 94 is a concentric inner tube 95 which provides a pathway for blood to flow into an absorbent tampon 97 which is proximal to the porous foam section 93. Prior to insertion, the tampon device 92 is enveloped in a sheath 98 which is necked down 99 between the porous foam section 93 and the bladder 96 so that, when the tampon device 92 is deployed and the sheath 98 moves over the bladder 96, the medication is forced out 101 through the perforated outer tube 94 into the porous foam section 93 (FIG. 17). The tampon device 92 includes a string 102 for removal of the tampon device 92.

Another example of a suitable controlled release drug delivery system for the present invention is the vaginal ring. Vaginal rings usually consist of an inert elastomer ring coated by another layer of elastomer containing the drug to be delivered. The rings can be easily inserted, left in place for the desired period of time (e.g., up to 7 days), then removed by the user. The ring can optionally include a third, outer, rate-controlling elastomer layer which contains no drug. Optionally, the third ring can contain a second drug for a dual release ring. The drug can be incorporated into polyethylene glycol throughout the silicone elastomer ring to act as a reservoir for drug to be delivered.

Pessaries, tablets and suppositories are other examples of drug delivery systems which can be used in the present invention. These systems have been used for delivery of vaginal medications and steroids, and have been described extensively in the literature.

Another example of a delivery system is the vaginal sponge. The desired pharmaceutical agent can be incorporated into a silicone matrix which is coated onto a cylindrical drug-free polyurethane vaginal sponge, as described in the literature.

Bioadhesive tablets are another drug delivery system. These bioadhesive systems use hydroxy propyl cellulose and polyacrylic acid. They release drugs for up to five days once they are placed in the appropriate formulation.

Bioadhesive microparticles contitute still another drug delivery system suitable for use in the present invention. This system is a multi-phase liquid or semi-solid preparation which does not seep from the vagina as do most current suppository formulations. The substances cling to the wall of the vagina and release the drug over a several hour period of time. Many of these systems were designed for nasal use but can be used in the vagina as well (e.g. U.S. Pat. No. 4,756,907). The system may comprise microspheres with an active drug and a surfactant for enhancing uptake of the drug. The microparticles have a diameter of 10–100 µm and can be prepared from starch, gelatin, albumin, collagen, or dextran.

The drug can also be incorporated into creams, lotions, foams, paste, ointments, and gels which can be applied to the vagina using an applicator. Processes for preparing pharmaceuticals in cream, lotion, foam, paste, ointment and gel formats can be found throughout the literature. An example of a suitable system is a standard fragrance free lotion formulation containing glycerol, ceramides, mineral oil, petrolatum, parabens, fragrance and water such as the product sold under the trademark JERGENS® (Andrew Jergens Co., Cincinnati, Ohio). This formulation was used by Hargrove et al. (Abstract No. 97,051, North American Menopause Society, Boston, Mass., September 1997) for transcutaneous delivery of estradiol and progesterone. Suitable nontoxic pharmaceutically acceptable systems for use in the compositions of the present invention will be apparent to those skilled in the art of pharmaceutical formulations and examples are described in REMINGTON'S PHARMACEUTICAL SCIENCES, 19$^{th}$ Edition, A. R. Gennaro, ed., 1995. The choice of suitable carriers will depend on the exact nature of the particular vaginal dosage form desired, e.g., whether the active ingredient(s) is/are to be formulated into a cream, lotion, foam, ointment, paste, solution, or gel, as well as on the identity of the active ingredient(s).

In practice, the drug delivery systems of the invention are applied several hours before or just after onset of menstruation in order to treat or prevent dysmenorrhea. The treatment would continue for a few hours up to 2 to 3 days, as needed, to alleviate and prevent painful menstruation and symptoms such as nausea, fatigue, diarrhea, lower backache, and headache.

Other features of the invention will become apparent in the course of the following descriptions of exemplary embodiments which are given for illustration of the invention and are not intended to be limiting thereof.

All references cited herein are hereby incorporated by reference in their entirety.

Procedures described in the past tense in the examples below have been carried out in the laboratory. Procedures described in the present tense have not been carried out in the laboratory, and are constructively reduced to practice with the filing of this application.

EXAMPLE 1

Preparation of Verapamil Vaginal Suppository

The dose of Verapamil (Sigma/Aldrich, St. Louis, Mo.) was 0.15–0.6 mg/kg body weight. Radioactively labeled Verapamil (4–7 µCi) was added to the unlabelled compound. Vaginal suppositories were formulated and prepared 24 hours prior to each experiment. The three basic ingredients for the suppositories were SUPPOCIRE® AS2 (Gattefosse, Westwood, N.J.) (75% wt); hydorxypropyl methylcellulose (e.g. METHOCEL® K, HPMC K15M) (Dow Chemical, Midland, Mich.) (10% wt), a mucoadhesive agent; and TRANSCUTOL® (Gattefosse) (15% wt). To make eight suppositories, 4.5 grams of SUPPOCIRE, 600 mg of HPMC, 900 mg of TRANSCUTOL, the calculated dose of the drug, and its labeled counterpart were weighed out. SUPPOCIRE was melted in a disposable 100 mL polypropylene beaker suspended in water at 50° C. The solution was stirred until completely melted. HPMC and TRANSCUTOL were then added and mixed. Finally, the unlabeled drug and the radioactively-labeled drug were added to the warm solution. The warm mixture was quickly poured into TYGON® tubing (available from Fisher Scientific, Pittsburgh, Pa.) molds (2 cm lengths), the tubing was kept upright on an ice-cold glass slab. Suppositories were kept refrigerated until use. The suppository was weighed prior to each experiment to determine the actual drug dose.

EXAMPLE 2

Preparation of Indomethacin Vaginal Suppository $^{14}$C-Indomethacin was obtained from Amersham Life Science, Arlington Hts., Ill. The dose of cold Indomethacin (Sigma/Aldrich) was 0.2 mg/kg body weight. Labeled Indomethacin (4–7 μCi) was added to the cold compound. All of the other steps in the preparation of the Indomethacin suppository are identical to those of Example 1 with Indomethacin replacing Verapamil.

EXAMPLE 3

Verapamil Pharmacokinetic Experiments $^3$H-Verapamil was obtained from DuPont/NEN, Boston, Mass. Prior to intravenous injection, cold Verapamil (Sigma/Aldrich, St. Louis, Mo.) (0.15–0.6 mg/kg body weight, i.v.) was dissolved in 0.5 mL dimethyl sulfoxide (Syntex, West Des Moines, Iowa). Labeled Verapamil (4–7 μCi) was then added to the cold compound just prior to i.v. injection.

Female white New Zealand rabbits weighing 2.8 to 3.5 kg were obtained from Myrtle Rabbitry (Thompson Station, Tenn.). Rabbits were kept in a National Institutes of Health approved facility and were acclimated to their environment at least 48 hours prior to each experiment.

Drug pharmacokinetic studies were performed via both the intravenous and transvaginal modes of administration. During the first series of experiments, the intravenous route of administration was utilized to determine the initial half-lives of the experimental compound. In the second series of experiments, the intravenous and transvaginal routes of administration were compared in the same rabbit.

After an 18 hour overnight fast, each rabbit was premedicated with ketamine (35 mg/kg, i.m.), xylazine (5 mg/kg, i.m.), and atropine (0.5 mg, i.m.). Each rabbit was intubated and anesthesia was maintained with isoflurane (1–3%). Vital signs were monitored throughout the experiment via a pulse oximeter. Rabbit body temperature was kept constant by a recirculating heating pad. Intravenous access was achieved by placement of a 22 gauge TEFLON catheter in the peripheral ear vein. Intra-arterial access was achieved by placement of a 22 gauge TEFLON catheter in the peripheral artery in the ear. A heat lamp was used to warm the ears to promote peripheral blood flow.

After the rabbit was anesthetized, the mixture containing labeled and unlabeled drug was injected through the ear vein over a 10 second to 2 minute period. Blood samples were drawn through the arterial line at 0.1, 0.25, 0.5, 0.75, 2, 4, 6, 8, 10, 12 and 24 hours relative to the time of injection. Blood samples (1 mL) were placed in a polypropylene tube containing EDTA. The blood was centrifuged at 2000 rpm for 10 minutes and 0.5 mL of plasma was placed into a scintillation vial.

0.1 to 0.2 gm uterine muscle biopsies were obtained at 0.2, 0.35, 0.5, 0.75, 2, 4, and 6 hours relative to drug administration from the uterine horn via a transverse laparatomy. For comparison purposes, gracilis muscle biopsies were taken at 1.5 and 6 hours relative to drug administration. Rabbits were euthanized with pentobarbital at the end of this experiment.

0.5 mL of Solvable tissue solubilizer (Packard, Meridian, Conn.) was added to the plasma samples and samples were vortexed for 30 seconds. 10 mL of Hionic-Fluor scintillation cocktail (Packard) was added and samples were vortexed for 1 minute.

1 mL of tissue solubilizer was added to tissue samples which were then placed in a shaking water bath at 50° C. to incubate overnight. 10 mL of scintillation cocktail (Packard) was added and samples were vortexed for 1 minute, then all samples were placed in the scintillation counter.

After the rabbit was anesthetized, labeled drug was injected through the ear vein as described above and blood samples were drawn at 0.1, 0.25, 0.5, 0.75, 2, 4, and 6 hours relative to the i.v. injection. The rabbit was allowed to recover and a 7-day washout period was carried out prior to the vaginal administration.

Vaginal suppositories were formulated and kept on ice. The suppository was introduced into the rabbit vagina using the barrel of a plastic transfer pipette (Baxter, McGaw Park, Ill.) and a tuberculin syringe as the plunger to load the suppository into the vagina to a depth of 7 to 8 cm. Blood samples were taken at 0.1, 0.25, 0.5, 0.75, 2, 4, and 6 hours relative to suppository administration. Uterine muscle and gracilis muscle biopsies were also obtained over the same time intervals using techniques as described previously.

Verapamil was administered as in Example 3. As shown in Table 1, blood levels persisted for a prolonged period of time, and the concentrating effect in the uterine muscle averaged up to 3.5 times that in gracilis muscle at several intervals. Table 1 is a summary of mean concentration ratios after intravaginal administration of Verapamil or Indomethicin.

TABLE 1

Mean Concentration (mcg/mL) Ratio's After Vaginal Administration

| Drug | At 0.5 hours: | At 1.5 hours: | At 6 hours: |
| --- | --- | --- | --- |
| Verapamil (n=5) | | | |
| Blood/Uterus | 0.72 | 0.67 | 1.51 |
| Blood/Leg | 1.52 | 1.58 | 1.75 |
| Uterus/Leg | 2.67 | 3.16 | 1.40 |
| Indomethacin (n=2) | | | |
| Blood/Uterus | 2.20 | 2.30 | 2.30 |
| Blood/Leg | 10.40 | 9.10 | 10.70 |
| Uterus/Leg | 4.75 | 4.00 | 4.70 |

Indomethacin was administered by the methods as described in hereinabove but with Indomethacin replacing Verapamil. The results (Table 1) demonstrated that the ratio of uterus to gracilis muscle concentration was 4 or 5 showing that after vaginal administration there were much higher concentrations in uterine tissue than in skeletal (gracilis) muscle. The results support the concept of selective and local delivery and uptake.

EXAMPLE 4

Preparation of a Solution Containing Naproxen for Intravaginal Application 120 mg of Naproxen is combined with 10 mg of Tween 80. That mixture is then combined with a quantity of isotonic saline sufficient to bring the total volume of the solution to 50 mL. The solution is sterilized by being passed through a 0.2 micron Millipore filter.

EXAMPLE 5

Preparation of a Gel Containing Naproxen for Intravaginal Application 250 mL of isotonic saline is heated to 80° C. and 1.50 grams of Methocel are added, with stirring. The resultant mixture is allowed to stand at room temperature for 2 hours. Then 120 mg of Naproxen is mixed together with 10 mg of Tween 80. The Naproxen/Tween mixture and a quantity of isotonic saline sufficient to bring the total volume to 500 mL were added to the gel and thoroughly mixed.

EXAMPLE 6

Preparation of Indomethacin Containing Lotion for Intravaginal Application

Indomethacin (I-7378, Sigma/Aldrich, St. Louis, Mo.) (50 mg) is added to one mL of JERGENS® standard fragrance free lotion.

EXAMPLE 7

Preparation of Ibuprofen Containing Gel for Intravaginal Application

Ibuprofen (I-4883, Sigma/Aldrich, St. Louis, Mo.) (200 mg) is added to one mL of gel comprised of the following ingredients: glycerin, mineral oil, polycarbophil, carbomer 934P, hydrogenated palm oil, glyceride, sodium hydroxide, sorbic acid, and purified water.

EXAMPLE 8

Preparation of Vaginal Suppositories

A vaginal suppository is prepared for intravaginal administration of each one of the following drugs at the indicated dose: Aspirin (975 mg), Piroxicam (20 mg), Indomethacin (50 mg), Fenamate (500 mg), Sulindac (200 mg), Nabumetone (750 mg), Ketorolac (10 mg), Ibuprofen (200 mg), Phenylbutazone (50 mg, P-8386, Sigma), Bromfenac (50 mg), Naproxen (550 mg), Lidocaine (100 mg), Mepivacaine (0.2 mg), Etidocaine (200 mg), Bupivacaine (100 mg), 2-Chloroprocaine hydrochloride (100 mg), Procaine (200 mg, P-9879, Sigma), Tetracaine hydrochloride (20 mg, T-7508, Sigma), Diltaizem (60 mg), Israpidine (10 mg), Nimodipine (30 mg), Felodipine (450 mg), Nifedipine (90 mg), Nicardipine (30 mg), Ritodrine (150 mg), Bepridil (300 mg), Dofetilide (1 mg), E-4031 (1 mg), Almokalant (1 mg), Sematilide (1 mg), Ambasilide (1 mg), Azimilide (1 mg), Tedisamil (100 mg), RP58866 (100 mg), Sotalol (240 mg), Ibutilide (1 mg), Terbutaline (5 mg), Salbutamol (1 mg), Piroxicam (20 mg), Metaproterenol sulphate (20 mg), nitroglycerin (3 mg), isosorbide dinitrate (40 mg) and isosorbide mononitrate (120 mg). All of the steps in the preparation of the drug suppository are identical to those of Example 1 except that no radiolabeled compound is used and the indicated amount of drug is used in place of Verapamil.

The quantity of vaginal dosage form needed to deliver the desired dose will of course depend on the concentration of the active ingredient in the composition. The therapeutic dosage range for vaginal administration of the compositions of the present invention will vary with the size of the patient.

EXAMPLE 9

Preparation of Other Compositions

A composition is prepared for intravaginal administration of each one of the following drugs at the indicated dose: Aspirin (975 mg), Piroxicam (20 mg), Indomethacin (50 mg), Fenamate (500 mg), Sulindac (200 mg), Nabumetone (750 mg), Ketorolac (10 mg), Ibuprofen (200 mg), Phenylbutazone (50 mg, P-8386, Sigma), Bromfenac (50 mg), Naproxen (550 mg), Lidocaine (100 mg), Mepivacaine (0.2 mg), Etidocaine (200 mg), Bupivacaine (100 mg), 2-Chloroprocaine hydrochloride (100 mg), Procaine (200 mg, P-9879, Sigma), Tetracaine hydrochloride (20 mg, T-7508, Sigma), Diltaizem (60 mg), Israpidine (10 mg), Nimodipine (30 mg), Felodipine (450 mg), Nifedipine (90 mg), Verapamil (120 mg), Nicardipine (30 mg), Ritodrine (150 mg), Bepridil (300 mg), Dofetilide (1 mg), E-4031 (1 mg), Almokalant (1 mg), Sematilide (1 mg), Ambasilide (1 mg), Azimilide (1 mg), Tedisamil (100 mg), RP58866 (100 mg), Sotalol (240 mg), Ibutilide (1 mg), Terbutaline (5 mg), Salbutamol (1 mg), Metaproterenol sulphate (20 mg), nitroglycerin (3 mg), isosorbide dinitrate (40 mg) and isosorbide mononitrate (120 mg). Each of the drugs listed in this example are substituted in Example 4, 5, 6 or 7, unless previously described, and repetition of the procedures there detailed affords other compositions according to the invention.

The quantity of vaginal dosage form needed to deliver the desired dose will of course depend on the concentration of the active ingredient in the composition. The therapeutic dosage range for intravaginal administration of the compositions of the present invention will vary with the size of the patient.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

The invention claimed is:

1. A method for transvaginal delivery of a pharmaceutically active agent into uterus, myometrium or endometrium for treatment of a human female patient comprising steps:

(a) providing an intravaginal ring, sponge, tampon or tampon-like device that maintains contact with the patient's vaginal epithelium, said device comprising a composition consisting essentially of:

a pharmaceutical agent absorbable through the vaginal epithelium;

wherein the pharmaceutical agent is selected from the group consisting of a nonsteroidal anti-inflammatory drug, a calcium channel blocker, a β-adrenergic agonist, a vasodilator and a drug capable of inhibiting dyskinetic muscle contraction;

wherein the amount of said composition applied to the vaginal epithelium is sufficient to deliver a therapeutically effective dose of the pharmaceutical agent to the uterine muscle of said female patient, and (b) delivering said device to the patient's vagina.

2. The method of claim 1 wherein said composition further comprises a mucoadhesive agent selected from the group consisting of alginate, pectin, and a cellulose derivative, a non-toxic excipient comprising a mixture of semisynthetic glycerides of saturated fatty acids of eight to eighteen carbons, and a penetration enhancing agent selected from the group consisting of a bile salt, an organic solvent, ethoxydiglycol and an interesterified stone oil.

3. The method of claim 2 wherein said nonsteroidal anti-inflammatory drug is selected from the group consisting of aspirin, ibuprofen, indomethacin, phenylbutazone, bromfenac, fenamate, sulindac, nabumetone, ketorolac, and naproxen; wherein said calcium channel blocker is selected from the group consisting of diltiazem, israpidine, nimodipine, felodipine, verapamil, nifedipine, nicardipine, and bepridil; and wherein said vasodilator is selected from the group consisting of nitroglycerin, isosorbide dinitrate, and isosorbide mononitrate.

4. The method of claim 3 wherein said device is the tampon, the tampon-like device the ring, or the sponge comprising the pharmaceutical agent formulated as a bioadhesive microparticle, an intravaginal cream, an intravaginal lotion, an intravaginal foam, an intravaginal paste, an intravaginal ointment, an intravaginal solution or an intravaginal gel.

5. The method of claim 3 wherein said agent is released from the device through a controlled release drug delivery system.

6. The method of claim 5 wherein said mucoadhesive agent is hydroxymethyl propylcellulose.

7. The method of claim 6 wherein said penetration enhancing agent is ethoxydiglycol or the interesterified stone oil.

8. The method of claim 7 wherein said composition comprises between about 60 to 90% by weight of the non-toxic excipient, between about 5 to 25% of the mucoadhesive agent, and between about 5 to 20% of the penetration enhancer.

9. The method of claim 5 wherein said controlled release drug delivery system comprises the intravaginal lotion comprised of glycerol, ceramides, mineral oil, petrolatum, parabens and water.

10. The method of claim 9 wherein said pharmaceutical agent is ketorolac.

11. The method of claim 9 wherein said pharmaceutical agent is verapamil.

12. The method of claim 9 wherein said pharmaceutical agent is indomethacin.

13. The method of claim 9 wherein said pharmaceutical agent is naproxen.

14. The method of claim 9 wherein said pharmaceutical agent is nitroglycerin.

15. A method for transvaginal delivery of the pharmaceutically active agent into uterus, myometrium or endometrium, comprising steps:
   (a) preparing a composition, in dosage unit form, for intravaginal delivery to a vaginal epithelium of a human female patient, said composition consisting essentially of:
      (i) an effective amount of a pharmaceutically active agent selected from the group consisting of a nonsteroidal anti-inflammatory drug, a calcium channel blocker, a β-adrenergic agonist, a vasodilator, and a drug capable of inhibiting dyskinetic muscle contraction;
      (ii) a mucoadhesive agent;
      (iii) a non-toxic excipient which promotes delivery through vaginal epithelium; and
      (iv) a penetration enhancing agent;
      wherein said composition is formulated to adhere and maintain contact with the vaginal epithelium;
      wherein said penetration enhancing agent enhances a transport of the pharmaceutical agent through the vaginal epithelium into the uterus, myometrium and endometrium; and
   (b) delivering or administering said composition into the patients' vagina using an intravaginal tampon, intravaginal tampon-like device, intravaginal ring or intravaginal sponge.

16. The method of claim 15 wherein said pharmaceutical agent is the nonsteroidal anti-inflammatory drug selected from the group consisting of aspirin, ibuprofen, indomethacin, phenylbutazone, bromfenac, fenamate, sulindac, nabumetone, ketorolac, and naproxen.

17. The method of claim 16 wherein said composition is formulated as an intravaginal bioadhesive tablet, intravaginal bioadhesive microparticle, intravaginal cream, intravaginal lotion, intravaginal foam, intravaginal ointment, intravaginal pasta, intravaginal solution, or intravaginal gel for delivery by the device of claim 15.

18. The method of claim 17 wherein said pharmaceutical agent is ketorolac, aspirin, ibuprofen, indomethacin or naproxen, wherein said mucoadhesive is hydroxypropyl methylcellulose, wherein said non-toxic excipient which promotes delivery of the pharmaceutical agent through the vaginal epithelium is a semisynthetic glyceride of saturated fatty acid of eight to eighteen carbons, and wherein said penetration enhancer is ethoxydiglycol or an interesterified stone oil.

19. The method of claim 18 wherein the composition comprises between about 5 to about 25% of the mucoadhesive agent, between 60 to about 90% of the non-toxic excipient and between about 5 to about 20% of penetration enhancer.

20. The method of claim 19 wherein the pharmaceutical agent is delivered into the uterus in an amount sufficient to treat dysmenorrhea.

21. The method of claim 20 wherein said pharmaceutical agent is indometacin.

22. The method of claim 20 wherein the pharmaceutical agent is ketorolac.

23. A method for transvaginal delivery of a pharmaceutically active agent into uterus, myometrium or endometrium for treatment of a human female patient comprising steps:
   (a) providing an intravaginal ring, sponge, tampon or tampon-like device that maintains contact with the patient's vaginal epithelium, said device comprising a composition comprising:
      a pharmaceutical agent absorbable through the vaginal epithelium;
      a pharmaceutically acceptable, non-toxic excipient which promotes delivery of the pharmaceutical agent through the vaginal epithelium;
      a mucoadhesive agent; and
      a penetration enhancing agent;
      wherein the pharmaceutical agent is selected from the group consisting of a nonsteroidal anti-inflammatory drug, a calcium channel blocker, a β-adrenergic agonist, a vasodilator and a drug capable of inhibiting dyskinetic muscle contraction;
      wherein the amount of said composition applied to the vaginal epithelium is sufficient to deliver a therapeutically effective dose of the pharmaceutical agent to the uterine muscle of said female patient, and
   (b) delivering said pharmaceutical agent to the patient transvaginally by release of the pharmaceutical agent from the composition comprised in the intravaginal device inserted into vagina.

* * * * *